(12) United States Patent
Bamber et al.

(10) Patent No.: US 10,982,414 B2
(45) Date of Patent: Apr. 20, 2021

(54) MINING SHOVEL WITH COMPOSITIONAL SENSORS

(71) Applicant: MineSense Technologies Ltd., Vancouver (CA)

(72) Inventors: Andrew Sherliker Bamber, Vancouver (CA); Ali Alatrash, Vancouver (CA); Igor Petrovic, Vancouver (CA); Greg Desaulniers, Vancouver (CA)

(73) Assignee: MineSense Technologies Ltd., Vancouver (CA)

( * ) Notice: Subject to any disclaimer, the term of this patent is extended or adjusted under 35 U.S.C. 154(b) by 0 days.

(21) Appl. No.: 16/028,222

(22) Filed: Jul. 5, 2018

(65) Prior Publication Data

US 2020/0018044 A1  Jan. 16, 2020

Related U.S. Application Data

(63) Continuation of application No. 15/351,071, filed on Nov. 14, 2016, now Pat. No. 10,036,142, which is a
(Continued)

(51) Int. Cl.
  *E02F 9/26* (2006.01)
  *E02F 9/20* (2006.01)
  (Continued)

(52) U.S. Cl.
  CPC .......... *E02F 9/26* (2013.01); *B07C 5/34* (2013.01); *B07C 5/36* (2013.01); *E02F 3/40* (2013.01);
  (Continued)

(58) Field of Classification Search
  CPC ...... E02F 9/26; E02F 3/40; B07C 5/34; B07C 5/36
  (Continued)

(56) References Cited

U.S. PATENT DOCUMENTS

| 719,343 A | 1/1903 | Langerfeld |
| 3,209,910 A | 10/1965 | Palmer |

(Continued)

FOREIGN PATENT DOCUMENTS

| AU | 2006249259 A1 | 6/2007 |
| CA | 2629408 A1 | 11/2009 |

(Continued)

OTHER PUBLICATIONS

Examination Report for Australian Patent Application 2012277493; dated Jul. 8, 2016, 4 pages.
(Continued)

*Primary Examiner* — Terrell H Matthews
(74) *Attorney, Agent, or Firm* — Perkins Coie LLP

(57) ABSTRACT

A mining shovel with compositional sensors comprises a bucket having various inward looking sensors positioned throughout the bucket. The bucket can also have disposed thereon a control enclosure that houses processing equipment that receives and analyzes the data collected by the inward looking sensors. The mining shovel with compositional sensors can be used as part of a system to manage a mining field, including generating and transmitting instructions directing where to deposit material located in the bucket based on the data collected from the inward looking sensors positioned in the bucket.

23 Claims, 7 Drawing Sheets

Related U.S. Application Data continuation of application No. 14/805,391, filed on Jul. 21, 2015, now Pat. No. 9,522,415.

(60) Provisional application No. 62/027,144, filed on Jul. 21, 2014.

(51) Int. Cl.
| | | |
|---|---|---|
| *B07C 5/34* | (2006.01) | |
| *E02F 3/40* | (2006.01) | |
| *B07C 5/36* | (2006.01) | |
| *G01N 33/24* | (2006.01) | |
| *E02F 3/407* | (2006.01) | |
| *E02F 3/30* | (2006.01) | |

(52) U.S. Cl.
CPC ............ *E02F 9/2054* (2013.01); *E02F 9/264* (2013.01); *E02F 9/265* (2013.01); *G01N 33/24* (2013.01); *E02F 3/308* (2013.01); *E02F 3/4075* (2013.01)

(58) Field of Classification Search
USPC ........................................ 209/420, 421, 552
See application file for complete search history.

(56) References Cited

U.S. PATENT DOCUMENTS

| | | | |
|---|---|---|---|
| 3,263,160 A | 7/1966 | Dolan et al. | |
| 3,337,328 A | 8/1967 | Lawyer | |
| 3,655,964 A | 4/1972 | Slight | |
| 3,701,419 A | 10/1972 | Nutter | |
| 3,747,755 A | 7/1973 | Senturia et al. | |
| 4,006,481 A | 2/1977 | Young et al. | |
| 4,030,026 A | 6/1977 | Payne | |
| 4,128,803 A | 12/1978 | Payne | |
| 4,236,640 A | 12/1980 | Knight | |
| 4,241,835 A | 12/1980 | Lockett | |
| 4,300,097 A | 11/1981 | Turner | |
| 4,361,238 A | 11/1982 | Kealy et al. | |
| 4,365,719 A | 12/1982 | Kelly | |
| 4,441,616 A | 4/1984 | Konig et al. | |
| 4,507,612 A | 3/1985 | Payne | |
| 4,600,356 A * | 7/1986 | Bridges .................. | E02F 9/245 172/6 |
| 4,659,989 A | 4/1987 | Kerr | |
| 4,909,930 A | 3/1990 | Cole | |
| 5,197,607 A | 3/1993 | Hakansson | |
| 5,236,092 A | 8/1993 | Krotkov | |
| 5,285,972 A | 2/1994 | Notebaart | |
| 5,413,222 A | 5/1995 | Holder | |
| 5,523,690 A | 6/1996 | Rowan | |
| 5,592,092 A | 1/1997 | Mechler | |
| 5,813,543 A | 9/1998 | Gesing et al. | |
| RE36,537 E | 2/2000 | Sommer et al. | |
| 6,078,018 A | 6/2000 | Davis et al. | |
| 6,444,936 B1 | 9/2002 | Ludwig et al. | |
| 6,545,240 B2 | 4/2003 | Kumar | |
| 6,664,914 B2 | 12/2003 | Longstaff et al. | |
| 6,693,274 B2 | 2/2004 | Baird | |
| 6,753,957 B1 | 6/2004 | Graft et al. | |
| 6,817,474 B2 | 11/2004 | Ikeda | |
| 7,161,672 B2 | 1/2007 | Gronushkin et al. | |
| 7,564,943 B2 | 7/2009 | Sommer et al. | |
| 7,574,821 B2 | 8/2009 | Furem | |
| 7,595,489 B2 | 9/2009 | Statham | |
| 7,737,379 B2 | 6/2010 | Witdouck | |
| 7,763,820 B1 | 7/2010 | Sommer et al. | |
| 7,786,401 B2 | 8/2010 | Valerio | |
| 7,797,861 B2 | 9/2010 | Wright | |
| 7,909,169 B1 | 3/2011 | Slade | |
| 7,948,237 B2 | 5/2011 | Kuzmin et al. | |
| 7,965,167 B2 | 6/2011 | Volker et al. | |
| 7,970,574 B2 | 6/2011 | Jin | |
| 8,100,581 B2 | 1/2012 | Djordjevic | |
| 8,138,437 B2 | 3/2012 | Valerio | |
| 8,315,838 B2 * | 11/2012 | Durrant-Whyte ....... | G06Q 10/06 703/1 |
| 8,446,156 B2 | 5/2013 | Morrison | |
| 8,494,220 B2 | 7/2013 | Del Grande | |
| 8,515,008 B2 | 8/2013 | Ulberg et al. | |
| 8,600,545 B2 | 12/2013 | Earlam | |
| 8,664,595 B2 | 3/2014 | Buhot et al. | |
| 8,766,129 B2 | 7/2014 | Kazakov et al. | |
| 8,812,149 B2 | 8/2014 | Doak | |
| 8,820,533 B2 | 9/2014 | Shaw et al. | |
| 8,843,266 B2 * | 9/2014 | Lindskov ................ | E02F 9/265 701/34.4 |
| 8,855,809 B2 | 10/2014 | Spencer et al. | |
| 8,875,901 B2 * | 11/2014 | Wellwood ............... | B07C 5/368 209/552 |
| 8,908,829 B2 | 12/2014 | Watanabe et al. | |
| 8,931,720 B2 | 1/2015 | Box et al. | |
| 8,937,282 B2 | 1/2015 | Owen et al. | |
| 8,957,340 B2 | 2/2015 | Wellwood et al. | |
| 8,958,905 B2 * | 2/2015 | Bamber .................. | E02F 9/265 700/223 |
| 9,010,543 B2 | 4/2015 | Box et al. | |
| 9,114,433 B2 | 8/2015 | Roos et al. | |
| 9,237,284 B2 | 1/2016 | Hogasten | |
| 9,290,913 B2 * | 3/2016 | Bamber .................. | B02C 23/08 |
| 9,314,823 B2 | 4/2016 | Bamber et al. | |
| 9,316,537 B2 | 4/2016 | Bamber et al. | |
| 9,764,361 B2 | 9/2017 | Valerio | |
| 9,884,346 B2 | 2/2018 | Bamber et al. | |
| 9,958,407 B2 | 5/2018 | Bamber et al. | |
| 10,029,284 B2 | 7/2018 | Bamber et al. | |
| 10,054,560 B2 | 8/2018 | Bamber et al. | |
| 10,259,015 B2 | 4/2019 | Bamber et al. | |
| 10,493,494 B2 | 12/2019 | Bamber et al. | |
| 2003/0009286 A1 | 1/2003 | Shibusawa | |
| 2004/0066890 A1 | 4/2004 | Dalmijn et al. | |
| 2005/0002029 A1 | 1/2005 | Gornushkin et al. | |
| 2005/0150844 A1 | 7/2005 | Hyndman | |
| 2005/0242006 A1 | 11/2005 | Bohlig | |
| 2006/0090379 A1 | 5/2006 | Furem | |
| 2006/0171504 A1 | 8/2006 | Sommer et al. | |
| 2007/0030953 A1 | 2/2007 | Sommer et al. | |
| 2008/0047170 A1 * | 2/2008 | Nichols .................. | G01S 19/45 37/348 |
| 2008/0192987 A1 | 8/2008 | Helgason et al. | |
| 2009/0076674 A1 | 3/2009 | Kiegeral et al. | |
| 2009/0322357 A1 | 12/2009 | Beaulieu | |
| 2010/0005926 A1 | 1/2010 | Valerio | |
| 2010/0091103 A1 | 4/2010 | Peltonen et al. | |
| 2011/0066404 A1 | 3/2011 | Salazar-Tio et al. | |
| 2011/0186660 A1 | 8/2011 | Harding et al. | |
| 2011/0313625 A1 * | 12/2011 | Miller .................... | E02F 3/3663 701/50 |
| 2012/0033212 A1 | 2/2012 | Barefield | |
| 2012/0046983 A1 | 2/2012 | Nettleton et al. | |
| 2012/0148018 A1 | 6/2012 | Sommer, Jr. | |
| 2013/0026263 A1 | 1/2013 | Bamber et al. | |
| 2013/0098807 A1 | 4/2013 | Wellwood et al. | |
| 2013/0126399 A1 | 5/2013 | Wolff | |
| 2013/0169961 A1 | 7/2013 | Kraft | |
| 2013/0201481 A1 | 8/2013 | Bamber et al. | |
| 2013/0272829 A1 * | 10/2013 | Innes ..................... | G01N 33/24 414/399 |
| 2013/0292307 A1 * | 11/2013 | Bamber ................ | B07C 5/3425 209/552 |
| 2013/0313169 A1 | 11/2013 | Lapeyre et al. | |
| 2014/0088876 A1 | 3/2014 | Shiley et al. | |
| 2014/0144342 A1 | 5/2014 | Bye | |
| 2014/0200054 A1 * | 7/2014 | Fraden ............. | H04M 1/72575 455/575.8 |
| 2014/0225416 A1 | 8/2014 | Harding et al. | |
| 2014/0260801 A1 * | 9/2014 | Wellwood ............ | G01N 25/005 75/392 |
| 2015/0004574 A1 * | 1/2015 | Bomer ..................... | G09B 9/04 434/219 |
| 2015/0085123 A1 * | 3/2015 | Tafazoli Bilandi ..... | G01S 17/86 348/148 |

(56) References Cited

U.S. PATENT DOCUMENTS

| | | | |
|---|---|---|---|
| 2015/0108258 | A1 | 4/2015 | Bamber et al. |
| 2016/0054044 | A1 | 2/2016 | Jeong et al. |
| 2016/0107197 | A1 | 4/2016 | Hartmann |
| 2016/0299116 | A1 | 10/2016 | Talmaki |
| 2017/0037594 | A1 | 2/2017 | Wada |
| 2017/0121945 | A1 | 5/2017 | Bamber et al. |
| 2019/0134671 | A1 | 5/2019 | Bamber et al. |
| 2019/0270122 | A1 | 9/2019 | Bamber et al. |
| 2020/0123732 | A1 * | 4/2020 | Hall ............... E02F 9/2883 |

FOREIGN PATENT DOCUMENTS

| | | | |
|---|---|---|---|
| CA | 2840545 A1 | 1/2013 | |
| DE | 3228447 C2 | 4/1986 | |
| EP | 2141414 | 1/2010 | |
| JP | S5389701 | 7/1978 | |
| JP | H0742201 | 2/1995 | |
| KR | 101402667 B1 * | 6/2014 | ............... E02F 9/12 |
| WO | 9530880 A1 | 11/1995 | |
| WO | WO9922870 A1 | 5/1999 | |
| WO | 2005085968 A1 | 9/2005 | |
| WO | WO2008046136 A1 | 4/2008 | |
| WO | 2008129115 A1 | 10/2008 | |
| WO | WO2009076674 A1 | 6/2009 | |
| WO | 2010028446 A1 | 3/2010 | |
| WO | WO2011116417 A1 | 9/2011 | |
| WO | WO2011120086 A1 | 10/2011 | |
| WO | WO2011134009 A1 | 11/2011 | |
| WO | WO2011150464 A1 | 12/2011 | |
| WO | 2013001364 A2 | 1/2013 | |
| WO | WO2013016774 A1 | 2/2013 | |
| WO | WO2013033572 A1 | 3/2013 | |
| WO | 2013163756 A1 | 11/2013 | |
| WO | 2016008059 A1 | 1/2016 | |

OTHER PUBLICATIONS

Examination Report for Australian Patent Application No. 2015292229, dated Apr. 3, 2018, 6 pages.
Examination Report for Australian Patent Application No. 2015292229, dated Oct. 13, 2017, 4 pages.
Examination Report for Australian Patent Application No. 2017202941, dated Jan. 12, 2018, 2 pages.
Examination Report for Canadian Patent Application 2,840,545; dated Mar. 23, 2016, 3 pages.
Extended European Search Report for European Application No. 12803664.7; dated Feb. 10, 2016, 17 pages.
Extended European Search Report for European Application No. 15824911.0, dated Jan. 31, 2018, 10 pages.
First Office Action in Chinese Patent Application 201580050857.7; dated Dec. 5, 2018, 9 pages, with English translation.
International Search Report and Written Opinion for International Application No. PCT/CA2015/050684, dated Sep. 30, 2015, 9 pages.
International Search Report and Written Opinion for International Application No. PCT/IB2012/001560, dated Nov. 29, 2012, 12 pages.
Office Action in Chile Patent Application No. 00164-2017, dated Apr. 5, 2018, 12 pages.
Office Action in Chile Patent Application No. 00164-2017, dated Sep. 12, 2018, 15 pages.
Partial Supplementary European Search Report for European Application No. 12803664.7, dated Oct. 16, 2015, 7 pages.
Second Examination Report for Australian Patent Application 2012277493, dated Sep. 27, 2016, 4 pages.
Singh et al., "Application of image processing and radial basis neural network techniques for ore sorting and ore classification," Minerals Engineering, vol. 18, Jan. 2005, 9 pages.
Supplementary European Search Report for European Application No. 12803664.7 dated Feb. 10, 2016, 11 pages.

Third Examination Report for Australian Patent Application 2012277493; dated Mar. 3, 2017, 4 pages.
Yang et al., "Electromagnetic conductivities of rock cores: Theory and analog results," Geophysics, vol. 62, No. 6, Nov.-Dec. 1997, 15 pages.
U.S. Appl. No. 16/027,612 for Bamber et al., filed Jul. 5, 2018.
Bamber, Andrew Sherliker, "Integrated Mining, Pre-Construction and Waste Disposal Systems for the Increased Sustainability of Hard Rock Metal Mining," Apr. 2008, pp. 29, 37-44, 85-89. <https://circle.ubc.ca/handle/2429/779>.
Examination Report for Australian Patent Application 2013255048; dated Jan. 21, 2016, 3 pages.
Examination Report for Australian Patent Application 2013255051; dated Jan. 27, 2016, 3 pages.
Examination Report for Australian Patent Application 2017201320; dated Mar. 28, 2018, 4 pages.
Examination Report for Australian Patent Application No. 2015292228, dated Oct. 4, 2017, 4 pages.
Examination Report for Australian Patent Application No. 2016216528, dated Nov. 2, 2017, 5 pages.
Examination Report for Australian Patent Application No. 2018214109, dated Oct. 9, 2019, 3 pages.
Examination Report for Australian Patent Application No. 2018203576, dated Jul. 30, 2019, 7 pages.
Examination Report for Australian Patent Application No. 2018241197, dated Nov. 14, 2019, 5 pages.
Examination Report for Australian Patent Application No. 2018204838, dated Aug. 8, 2019, 4 pages.
Examination Report for European Patent Application No. 13784189.6, dated Apr. 23, 2019, 3 pages.
Examination Report for European Patent Application No. 13784899.0, dated Jun. 20, 2017, 3 pages.
Examination Report for European Patent Application No. 15824911.0, dated Jul. 18, 2019, 5 pages.
Examination Report for European Patent Application No. 18166364.2, dated Nov. 6, 2019, 3 pages.
Examination Report for European Patent Application No. 15824840.1, dated Nov. 6, 2019, 6 pages.
Extended European Search Report for European Application No. 13784189.6; dated Nov. 5, 2015, 7 pages.
Extended European Search Report for European Application No. 13784899.0; dated Jun. 10, 2016, 11 pages.
Extended European Search Report for European Patent Application No. 15824840.1, dated Mar. 8, 2018, 5 pages.
Extended European Search Report for European Patent Application No. 18166364.2, dated Jul. 10, 2018, 6 pages.
First Office Action in Chilean Patent Application No. 2017-00150; dated Jun. 20, 2018, 7 pages.
First Office Action in Chinese Patent Application 201580050856.21; dated May 3, 2018, 23 pages, with English translation.
First Official Action in Chilean Patent Application 2924-2014, dated Oct. 29, 2014, 5 pages.
First Official Action in Chilean Patent Application 2925-2014, dated Oct. 29, 2014, 5 pages.
International Search Report and Written Opinion for International Application No. PCT/CA2013/050330, dated Jul. 24, 2013, 9 pages.
International Search Report and Written Opinion for International Application No. PCT/CA2013/050336, dated Aug. 12, 2013, 12 pages.
International Search Report and Written Opinion for International Application No. PCT/CA2015/050683; dated Oct. 21, 2015, 7 pages.
Kieba et al. "Differential Soil Impedance Obstacle Detection," U.S. Department of Energy Technical Report No. DE-FC26-02NT41318, Report Issue Date Jan. 17, 2005, 72 pages.
N. G. Cutmore et al., "Ore Characterisation and Sorting," Minerals Engineering, vol. 10, No. 4., Jan. 1997, 6 pages.
Partial Supplementary European Search Report for European Application No. 13784899.0, dated Feb. 16, 2016, 7 pages.
Second Examination Report for Australian Patent Application No. 201592228, dated Feb. 28, 2018, 4 pages.
Second Office Action for Chilean Patent Application No. 2924-2014, dated Jan. 7, 2017, 5 pages.

(56) References Cited

OTHER PUBLICATIONS

Second Office Action for Chilean Patent Application No. 2925-2014, dated Feb. 25, 2017, 5 pages.
Second Office Action in Chilean Patent Application No. 2017-00150; dated Feb. 13, 2019, 7 pages.
Supplementary European Search Report for European Application No. 13784899.0; dated Feb. 16, 2016, 7 pages.
Examination Report for Australian Patent Application No. 2019204043, dated May 17, 2020, 5 pages.
Extended European Search Report for European Application No. 20165382.1; dated Jul. 27, 2020, 9 pages.
Second Office Action in Chinese Patent Application 201580050857.7; dated Jul. 31, 2019, 8 pages.
Third Office Action in Chinese Patent Application 201580050857.7; dated May 29, 2020, 4 pages.
Extended European Search Report for European Patent Application No. 20160983.1, dated Oct. 2, 2020, 7 pages.
First Office Action in Chinese Patent Application 201910037844.6; dated Sep. 27, 2020, 11 pages.
Second Examination Report for Australian Patent Application No. 2018214109, dated Jun. 11, 2020, 3 pages.
Third Examination Report for Australian Patent Application No. 2018214109, dated Oct. 1, 2020, 5 pages.

\* cited by examiner

MINING SHOVEL WITH COMPOSITIONAL SENSORS

CROSS-REFERENCE TO RELATED APPLICATIONS

This application is a continuation of U.S. application Ser. No. 15/351,071, filed Nov. 14, 2016, which is a continuation of U.S. application Ser. No. 14/805,391, filed Jul. 21, 2015, which claims the benefit under 35 U.S.C. § 119(e) of U.S. Provisional Application No. 62/027,144, filed Jul. 21, 2014, entitled "Mining Shovel With Compositional Sensors", which is hereby incorporated by reference for all purposes in its entirety.

BACKGROUND

In the field of mineral sorting, sorting machines generally comprise a single stage of sensor arrays controlling (via, e.g., micro controller or other digital control system) a matched array of diverters.

Sensors used in mineral sorting can be of diverse origin, including photometric (light source and detector), radiometric (radiation detector), electromagnetic (source and detector or induced potential), or more high-energy electromagnetic source/detectors such as x-ray source (fluorescence or transmission) or gamma-ray source types. Matched sensor/diverter arrays are typically mounted onto a substrate (e.g., vibrating feeder, belt conveyor, free-fall type), which substrate transports the material to be sorted past the sensors and thus on to the diverters where the material is diverted to either one of two destinations, 'accept' or 'reject'.

Sorting is typically undertaken by one or more high-efficiency machines in a single stage, or in more sophisticated arrangements, such as rougher/scavenger, rougher/cleaner, or rougher/cleaner/scavenger. Material to be sorted is typically metallic mineral material between 15 mm-200 mm in size, although finer and coarser materials can be sorted with smaller or larger machines as the case may be.

Sorter capacity is limited by several factors, including micro controller speed, belt or feeder width, and a typical requirement to a) segregate the feed over a limited particle size range, and b) separate individual particles in the feed from each other prior to sorting to ensure high efficiency separation. A new type of sorting with high effectiveness in the mining industry comprises in-mine batch mineral sensing and classification. However, further advancements are still needed before such in-mine batch sorting devices can be successfully operated in the field.

BRIEF DESCRIPTION OF THE DRAWINGS

Embodiments of the present disclosure will be described and explained through the use of the accompanying drawings in which.

Figure 1:
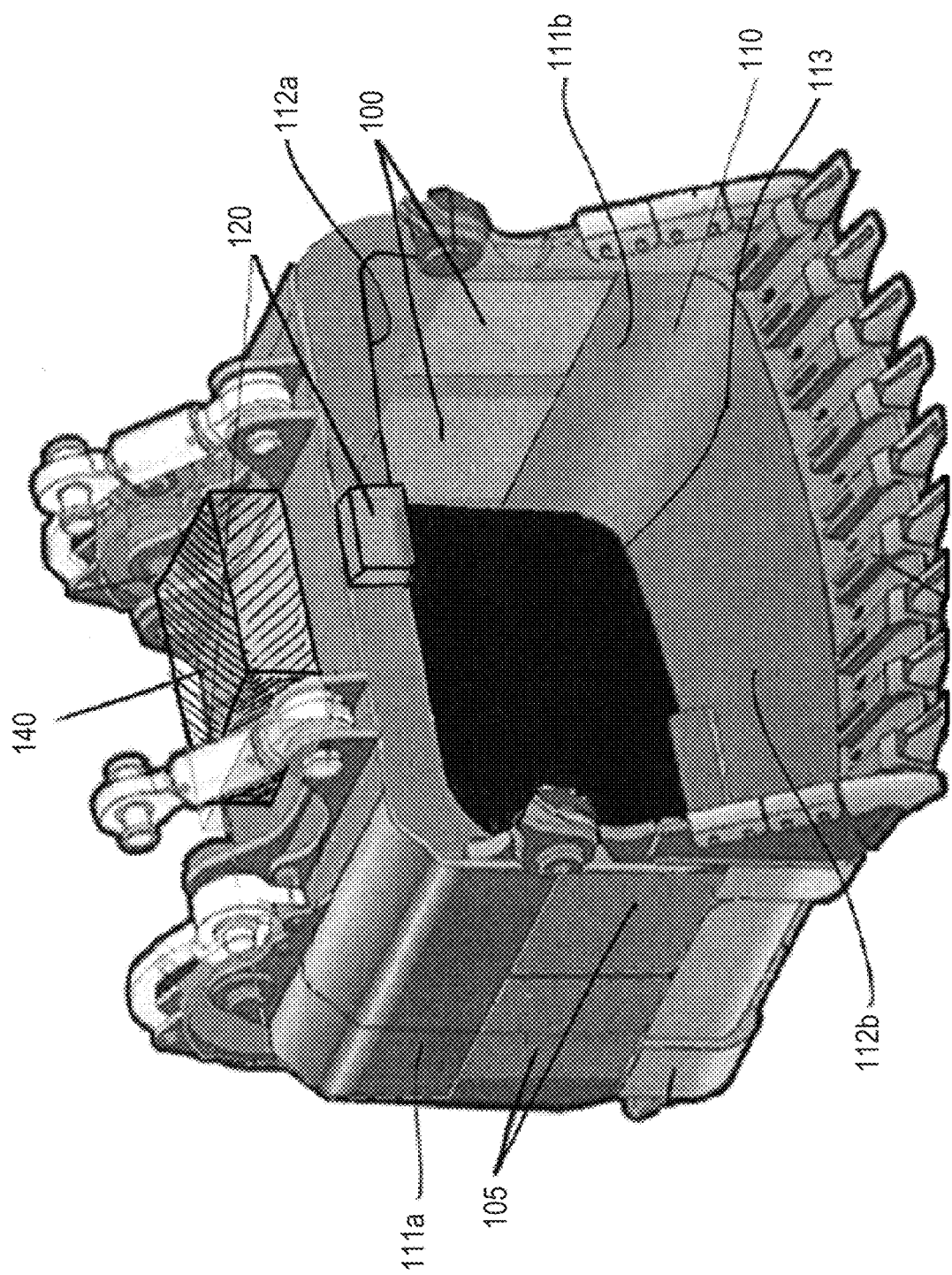
FIG. 1 is an illustration of a mining shovel bucket having inwardly facing sensors positioned thereon in accordance with various embodiments described herein.

The drawings have not necessarily been drawn to scale. For example, the dimensions of some of the elements of the figures may be expanded or reduced to help improve the understanding of the embodiments of the present application. Similarly, some components and/or operations may be separated into different blocks or combined into a single block for the purposes of discussion of some of the embodiments of the present application. Moreover, while the disclosure is amenable to various modification and alternative forms, specific embodiments have been show by way of example in the drawings and are described in detail below. The intention, however, is not to limit the disclosure to the particular embodiments described. On the contrary, the disclosure is intended to cover all modifications, equivalents, and alternatives falling within the scope of the disclosure.

DETAILED DESCRIPTION

Disclosed herein are various embodiments of mining shovel a mining shovel with composition sensors, methods of sorting material using a mining shovel with compositional sensors, and systems incorporating a mining shovel with compositional sensors. In some embodiments, the mining shovel comprises a bucket having various inward looking sensors positioned throughout the bucket. The inward looking sensors can include one or more in-cheek sensors positioned on a side wall of the bucket and/or one or more downward looking sensors positioned on an upper wall portion of the bucket. The bucket can also have disposed thereon a control enclosure used for housing various processing equipment that receives and analyzes the data collected by the inward looking sensors. In some embodiments, the processing equipment is used to identify the chemical composition of the material located in the bucket of the mining shovel.

In some embodiments, the mining shovel with compositional sensors is part of a system used in field operations to direct where material located in the bucket should be transported. In addition to the bucket described above, the system can include additional signal processing equipment located remote from the bucket, such as in the chassis of the mining shovel, and communications links between the signal processing equipment in the bucket and the signal processing equipment in the chassis. In this manner, data can be relayed from the bucket to the chassis, where, for example, further data analysis can be carried out. The system can further include an operator's enterprise resource planning (ERP) system, a fleet management system, and/or communications links for transmitting information between all of the components of the system. In some embodiments, predetermined values relating to identification of material composition is stored in a database that is part of the ERP system, such that data transmitted to the ERP system from the bucket and/or chassis can be compared against the database to match patterns and thereby identify material composition. Once material composition is identified, signals can be sent from the ERP system to the fleet management system so that a determination of where to transport the material in the bucket can be made. The decision made by the fleet management system can subsequently be communicated to, for example, a local display located in the chassis of the mining shovel so that a shovel operator can deposit the bucket material in the appropriate location.

In some embodiments, a method of in-mine sensing and classification generally includes sensing material in a mining shovel bucket using one or more inward facing sensors positioned in the bucket and transmitting the data obtained from sensing the material to signal processing equipment. The method can further include identifying the composition of the material by processing the data with signal processing equipment. Once identified, the method can further includes transmitting an instruction of where to transport the bucket material, such as to a mining shovel operator. Destination instructions can also be sent to a haul truck which receives the material from the mining shovel.

Various embodiments will now be described. The following description provides specific details for a thorough understanding and enabling description of these embodiments. One skilled in the art will understand, however, that the invention may be practiced without many of these details. Additionally, some well-known structures or functions may not be shown or described in detail, so as to avoid unnecessarily obscuring the relevant description of the various embodiments.

The terminology used in the description presented below is intended to be interpreted in its broadest reasonable manner, even though it is being used in conjunction with a detailed description of certain specific embodiments of the invention. Certain terms may even be emphasized below; however, any terminology intended to be interpreted in any restricted manner will be overtly and specifically defined as such in this Detailed Description section.

With reference to FIG. 1, a mining shovel bucket 110 generally includes a first side wall 111*a*, a second side wall 111*b* opposite the first side wall 111*a*, an upper wall portion 112*a*, a lower wall portion 112*b* opposite the upper wall portion 112*a*, and a back wall portion 113. The first side wall 111*a*, second side wall 111*b*, upper wall portion 112*a*, lower wall portion 112*b*, and a back wall portion 113 generally define an interior volume of the bucket 110 into which material can be scooped and held. The bucket 110 may generally be any type of bucket suitable for use in mining shovel operations, including buckets of varying shapes, sizes, and materials.

The mining shovel bucket further includes one or more sensors, such as an in-cheek sensor 100 on the first side wall 111*a* and an in-cheek sensor 105 on the second side wall 111*b*. Each in-cheek sensor 100, 105 faces towards the interior volume so that material within the interior volume can be subjected to sensing by the sensors 100, 105. The in-cheek sensors 100, 105 can be any type of sensor suitable for use in analyzing and collecting data on mining material that can subsequently be used in determining the composition of the mining material. Suitable sensors include, but are not limited to radiometric, photometric, and electromagnetic sensors. While FIG. 1 shows one in-cheek sensor per side wall, the bucket may include any number of in-cheek sensors. In some embodiments, only a single in-cheek sensor is provided on one side wall, while the other side wall does not include an in-cheek sensor. In some embodiments, only one side wall includes an in-cheek sensor, but includes more than one in-cheek sensor. In some embodiments, both side walls include more than one in-cheek sensor. In some embodiments, each side wall includes the same number of in-cheek sensors, while in some embodiments, the side walls include a different number of in-cheek sensors. The in-cheek sensors may all be the same type of sensor, or the in-cheek sensors can be any combination of different types of sensors.

Alternatively or additionally, the mining shovel bucket further includes at least one down looking sensor 120 positioned on the upper wall portion 112*a*. The down looking sensor 120 is positioned to face toward the interior volume so that material within the interior volume can be subjected to sensing by the down looking sensor 120. The down looking sensor 120 can be any type of sensor suitable for use in analyzing and collecting data on mining material that can subsequently be used in determining the composition of the mining material. Suitable sensors include, but are not limited to radiometric, photometric, and electromagnetic sensors. While FIG. 1 shows a single down-looking sensor positioned at a forward portion of the upper wall portion 112*a*, the bucket may include any number of down looking sensors arranged throughout the upper wall portion 112*a*. In some embodiments, the bucket includes a down looking sensor 120 in a forward position of the upper wall portion 112*a* as shown in FIG. 1, as well as a down looking sensor 120 in an aft position of the upper wall portion 112*a* (i.e., proximate where the upper wall portion 112*a* contacts the back wall portion 113. When multiple down looking sensors are included, the sensors may all be the same type of sensor, or may be any combination of different types of sensors. While not shown, if the material of the mining shovel bucket interferes with operation of the sensors (e.g., as might happen with certain type of metals), the sensors may be mounted inside of the bucket, and have formed thereon a ruggedized, non-metallic layer, such as one of vulcanized rubber or other rugged, non-conductive elastomeric material.

With continuing reference to FIG. 1, the bucket 110 may include a control enclosure 140. The control enclosure may be mounted on any exterior surface of the bucket 110. As shown in FIG. 1, the control enclosure 140 is mounted on a top exterior surface of the bucket 110. The size, shape, and material of the enclosure 140 is generally not limited, and typically selected such that it can safely accommodate and protect the various equipment that can reside therein.

The control enclosure 140 can house a wide variety of equipment used in carrying out the sensing of mining material loaded in the interior volume of the bucket 110. In some embodiments, the enclosure 140 houses signal processing equipment. The signal processing equipment is generally used to receive signals from the sensors 100, 105, 120 and partially or fully process the signals to identify the composition of the material loaded in the bucket. The enclosure 140 can also house communications components suitable for use in transmitting signals from the bucket to locations remote to the bucket (for example, the chassis of the mining shovel, remote stations on the mining operation field, etc.). Any suitable communication components can be used to transmit signals from the bucket to a remote location. In some embodiments, the communications components housed in the enclosure 140 are wireless communications components for wireless delivering signals to remote locations. The enclosure 140 can further house sensor electronics that are part of sensors 100, 105, 120, as well as power components (e.g., batteries) needed to power the various sensors, signal processing equipment, communication components, etc.

Figure 3:
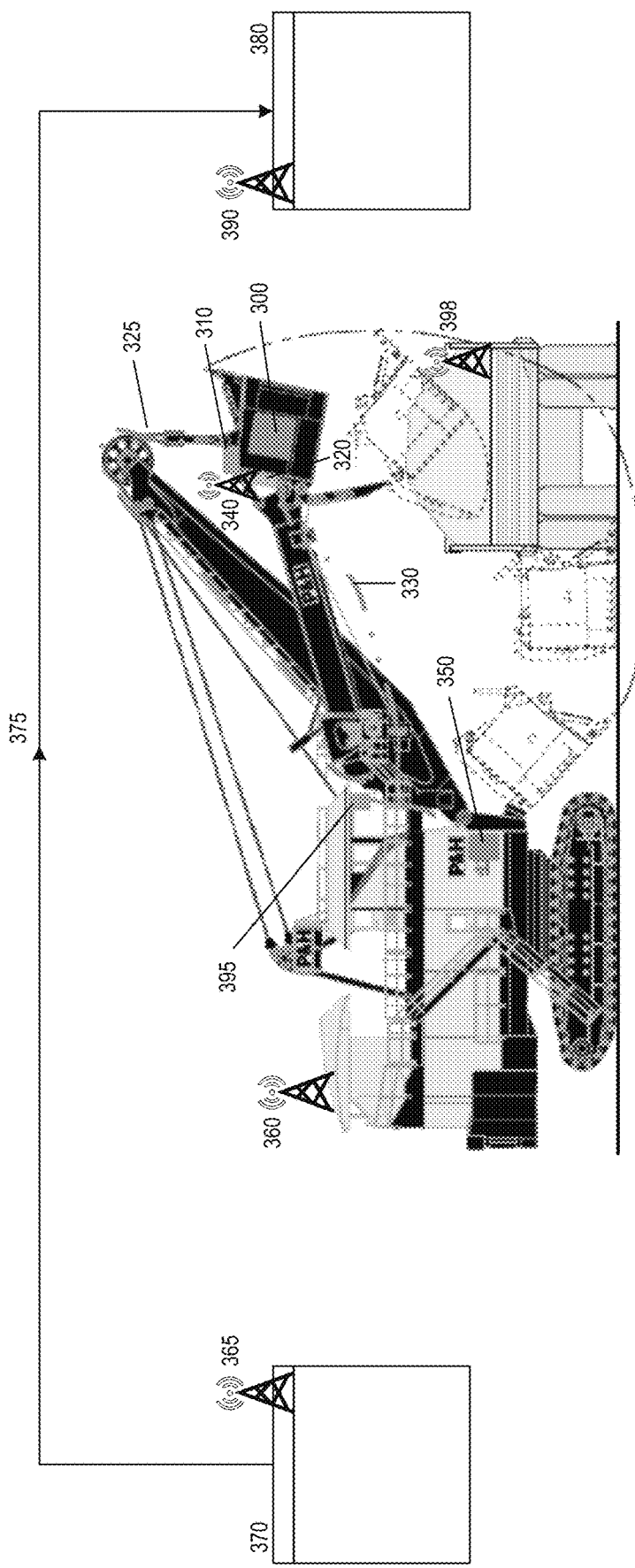
FIG. 3 is a schematic illustration of a mining sensing and sorting system in accordance with various embodiments described herein.

With reference to FIG. 3, a system 300 incorporating the bucket with compositional sensors described above and suitable for use in sensing and classifying mining material is illustrated. The system 300 generally includes a mining shovel 302 comprising a bucket 110 as described above in FIG. 1 and a chassis 303, a mine operator's enterprise resource planning (EPR) system 370, and a mine fleet management system 380.

The mining shovel 302 is generally any type of mining shovel suitable for use in the excavation of mining material in a field operation. The mining shovel 302 can be, for example, a wire rope type or a hydraulic excavator type mining shovel. In addition to including the bucket 110 having interior volume facing sensors 100/105/120, the mining shovel 302 also includes a chassis 303. The chassis 303, amongst other things, includes an operator's cabin where an operator controls the mining shovel 302.

As shown in FIG. 3, the bucket 110 can be incorporated with the mining shovel via, for example, fiber optic communication cable 325, power supply cable 330, and wireless data communication 340, all of which are specifically incorporated with the various equipment included within the control enclosure 140. The fiber optic communication cable 325 and/or the wireless data communication 340 can be used to communicate between the processing equipment within the control housing 140 and additional processing equipment located remote from the bucket 110. For example, as shown in FIG. 3, the chassis 303 includes an enclosure 350 that may house any additional processing equipment needed for the purpose of processing and analyzing data collected by the sensors 100/105/120 that is not present in the control housing 140. In some embodiments, the processing equipment need for processing and analyzing signals from the sensors 100/105/120 is divided amongst the various housings due to space constraints, power demands, system optimization, etc. When communication between the equipment within the control housing 140 and the equipment within the enclosure 350 is carried out wirelessly, the chassis 303 can further include a wireless node 360 for receiving wireless transmission from the wireless data communication 340. The wireless node 360 can also be used to communicating data processed within the enclosure 350 to other parts of the system 300.

In some embodiments, data processed within the enclosure 350 and/or the control housing 140 is transmitted to a mine operator's enterprise resource planning (ERP) system 370 located remote from the mining shovel (such as in trailers set up at mining operations for various logistical requirements). ERP systems are generally used in mining operations to help ensure that mining material is directed to the appropriate destination based on a variety of variable conditions (e.g., commodity prices). For example, in some embodiments, ERP systems can be used to help direct higher quality mining material to product streams when commodity prices are low, while directing medium and lower quality mining material to waste or holding piles. Conversely, the ERP system can be used to help direct higher and medium quality mining material to product streams when commodity prices are high, while directing low quality mining material to waste or holding piles.

The ERP system 370 can include a wireless transceiver for receiving data from the processing equipment in the enclosure 350 and/or control housing 140 and subsequently transmitting additional information on to other parts of the system 300. In some embodiments, the ERP system 370 is specifically used to carry out the part of the data processing in which data from the shovel (which may be raw data or pre-processed data) is compared against predetermined values stored in a short range mine plan database that is part of the ERP system. The remotely located ERP system is well suited for such a database due to logistical issues previously noted, such storage capacity and processing demands which are difficult to meet in the smaller, remotely located enclosure 350 and/or housing 140. Once the database and ERP system have been utilized to make a final determination as to material composition within the bucket, the ERP system can subsequently be used to transmit this information to other parts of the system 300. In some embodiments, the wireless transceiver 365 is used in conjunction with a mine operators network 375 to transmit the information throughout the system 300.

The system 300 can further include a fleet management system 380 used to manage mine operations specifically with respect to mine shovel operation and the various trucks used on site to transport material. Fleet management systems are generally used to help direct the movement of one or more mining shovels and one or more fleet trucks within a specific mining operation to help maximize operation of the mining operation. For example, in a mining operation where more than one mining material is being recovered, a mining shovel having a bucket full or material found to include more of a first material than a second material can be directed to deposit the material in a specific haul truck via the fleet management system. The fleet management system can subsequently direct the haul truck to specific location based on the contents previously deposited therein.

In some embodiments, the information generated by the ERP system with respect to the composition of the material in the bucket 110 is transmitted to the fleet management system 380 so that a determination as to where the material in the bucket 110 should be deposited. In a scenario where the material in the bucket 110 has been determined to be of a desirable composition, the fleet management system 380 can be used to direct the material to be deposited in a haul truck used for transporting desirable material to a desired location (e.g., storage or further processing). In a scenario where the material in the bucket 110 has been determined to be waste material, the fleet management system 380 can be used to direct the material to be deposited in a haul truck used for transporting waste material to a specific location or to direct the mining shovel operator to directly deposit the waste material in a nearby waste pit or on a nearby waste pile.

To further facilitate these types of directions, the system may further include a local display 395 in the mining shovel chassis 303. The fleet management system 380 having made a determination as to where the material in the bucket 110 should be deposited can transmit directions to the local display 395 (e.g., such as through wireless communications) in the chassis 303. The mining shovel operator can subsequently use the directions provided on the local display 395 to make the correct operations with respect to transporting and depositing the material in the bucket 110. Similarly, the system can further include a local display 398 in the cabin of a haul vehicle 399 used on site. Similar information as to what is delivered to the local display 395 in the mining shovel chassis 303 can be delivered to the haul truck 399 via the local display 398 so that the operator of the haul truck 399 can both make the haul truck 399 available to the mining shovel 302 for depositing material and get information on where to transport the material once it is loaded on the haul truck 399.

Figure 2:
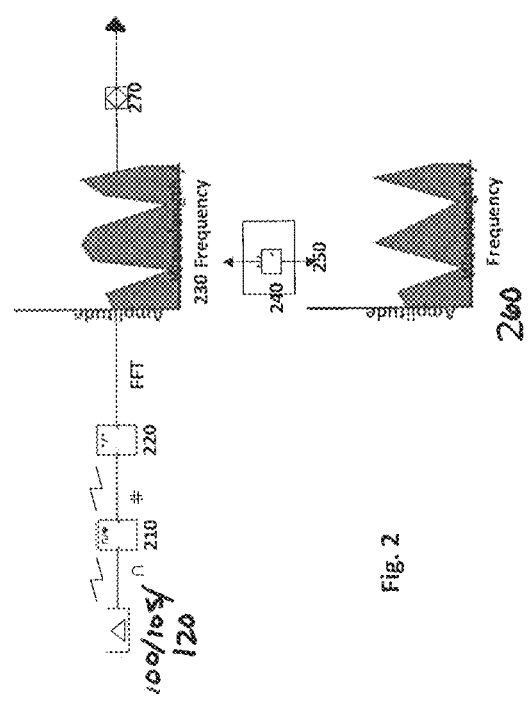
FIG. 2 is a schematic illustration of a sensor array in accordance with various embodiments described herein.

As discussed above, the system 300 generally includes various signal processing equipment configured to receive and analyze data from the sensors 100/105/120 for the purpose of identifying the composition of the material in the bucket 110. With reference to FIG. 2, a system and method of analyzing the data according to various embodiments is illustrated. The system and method may begin by converting signals of arbitrary waveform and frequency from the sensors 100/105/120 from analogue to digital using, for example, an analogue to digital signal converter 210. Any analogue to digital converter suitable for converting analogue signals from the sensors to digital signals may be used. In some embodiments, the sensors 100/105/120 produce digital signals in the first instance, in which case an analogue to digital signal converter 210 may not be required in the system and method.

Once digital signals are available, the method and system can include a step of passing the digital signals to a Fourier Analysis stage. The Fourier Analysis stage can generally include using a field programmable gate array 220 to generate spectral data 230 of amplitude/frequency or amplitude/wavelength format via Fast Fourier Transform (FFT) implemented on the field programmable gate array 220. The arbitrary power spectra 230 generated in the Fourier Analysis stage (via the field programmable gate array 220) are compared to previously determined and known spectra 260, which may be stored in the short range mine plan database referenced above as being part of the ERP system 370. The comparison between the generated power spectra 230 and the known spectra 260 can be carried out using a pattern matching algorithm 240 running on an embedded computer 250. The pattern matching algorithm 240 works to recognize arbitrary power spectra 230 that match the spectra of desired material based on the predetermined and known spectra of the desired material. The result of the matching algorithm 240 results in the generation and transmission of an instruction 270 by the embedded computer 250. The instruction 270 can generally be an "accept" instruction or a "reject" instruction. When a match to the spectra of desirable material is made, "accept" instructions are generated. When the algorithm 240 fails to make a match to the spectra of desirable material or a match to the spectra of undesirable material is made, "reject" instructions are generated. The accept or reject instruction 270 can subsequently be sent to, for example, the fleet management system 380 mentioned above with respect to FIG. 3 so that appropriate direction can then be given to the mining shovel operator (via, e.g., local display 395 in mining shovel chassis 303) and/or the haul truck operator (via, e.g., local display 398 in haul truck 399). In some embodiments, the instructions 270 can be sent directly to the mining shovel operator and/or haul truck operator.

The performance of the steps described in FIG. 2 can be carried out in any combination of locations throughout the system 300 illustrated in FIG. 3. In some embodiments, the only step of the data analysis carried out at the bucket 110 (i.e., within the control housing 140) is the conversion of the analogue signal to a digital signal. In such embodiments, steps such as generating power spectra, comparing the arbitrary power spectra to known spectra, establishing matches between the arbitrary power spectra and the known spectra, and generating and transmitting accept or reject instructions may be carried out at, for example, the chassis 303 (such as within the enclosure 350), the ERP system 370, and/or the fleet management system 380 in any combination. Alternatively, additional or all steps of the data analysis other than conversion from analogue to digital signals are carried out at the bucket 110, in which case fewer or no data analysis steps are carried out in the other locations of the system 300.

Figure 4:
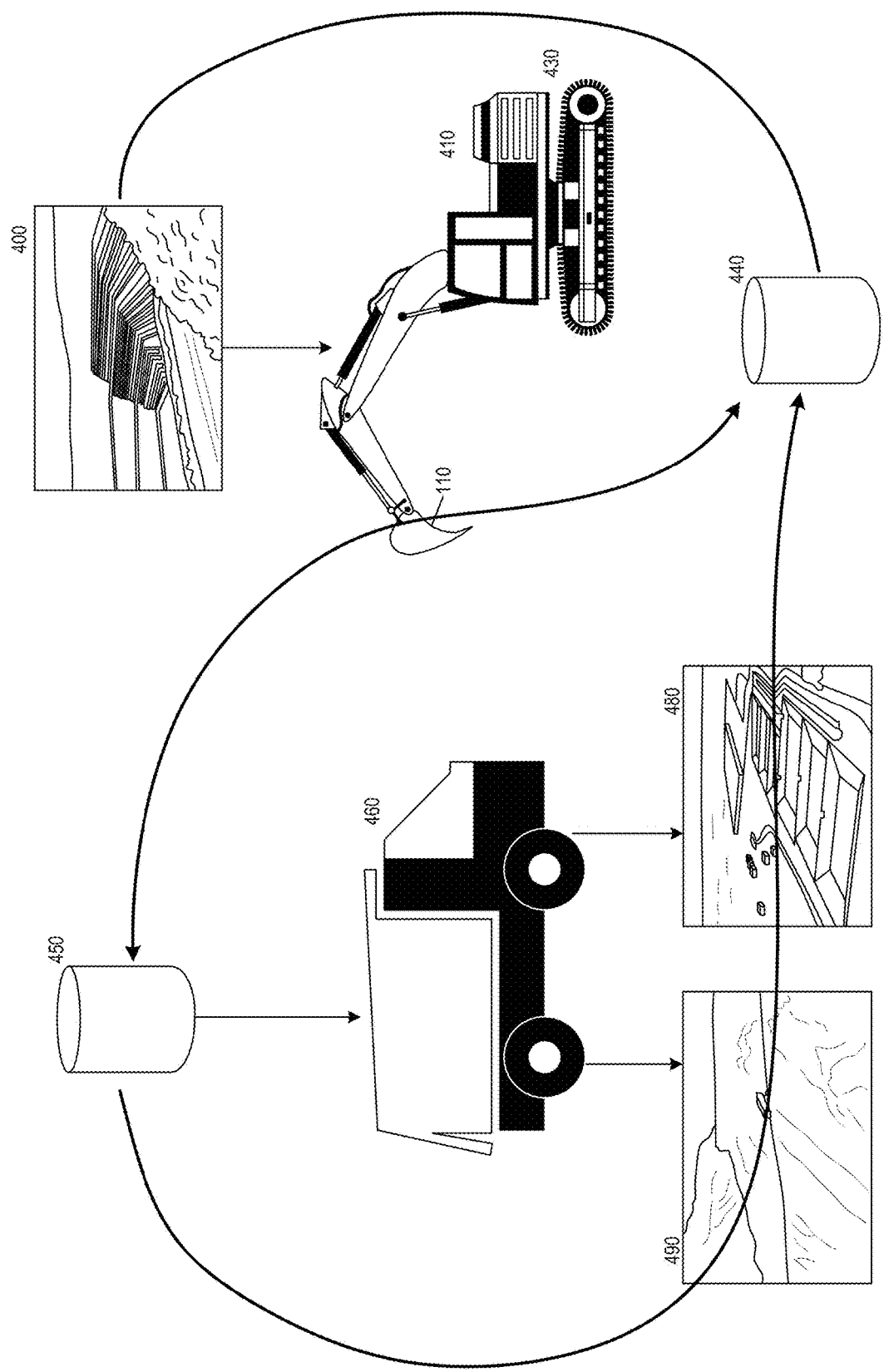
FIG. 4 is an illustration of a method of sensing and sorting mining material in accordance with various embodiments described herein.

With reference now to FIG. 4, an illustrated method of carrying out sensing, classification, and sorting of mining material using the bucket with compositional sensors described herein is shown. The method generally begins with excavating a bench or stope of mineral material 400 using a mining shovel or loader 410 including a bucket with compositional sensors 110 as described herein. Once the bucket is loaded with mining material, the sensors in the bucket 110 are used to sense the material and gather data about the material loaded in the bucket 110. The results of these measurements are conveyed to the mine planning system 440 (also referred to as the ERP system 370 in FIG. 3) via, e.g., an on-shovel wireless communication node 430. Once received by the mine planning system 440, the values from the bucket 110 are compared to stored values in the mine planning system 440 to find matches that identify the composition of the material. When a match to desirable material is made, instructions to accept the material in the bucket 110 are conveyed to the fleet management/ore routing system 450 via, e.g., a mine operators network or communications network. When a match to desirable material is not found, or when a match to undesirable material is made, instructions to reject the material in the bucket 110 are conveyed to the fleet management/ore routing system 450.

From the fleet management system 450, instructions on where to deliver the material based on the accept or reject instructions are transmitted to the shovel operator and/or haul truck operator. The shovel operator receiving an accept instruction may deliver the material either to a haul truck 460 that further transports the desired material to a specified location (e.g., a leach area 480), or directly to an area proximate the mining shovel where desired material is being stored or processed (e.g., the leach area 480). The shovel operator receiving a reject instruction may deliver the material either to a haul truck that further transports the undesired material to a specified location (e.g., a dump area 480) or directly to an area proximate the mining shovel where undesired material is being stored (e.g., a dump area 480). Overall, the present system integrates the sensor technology with the ERP system 370 and fleet management system 450 to thereby efficiently extract and process desired minerals/materials from a mine or other location.

Figure 5:
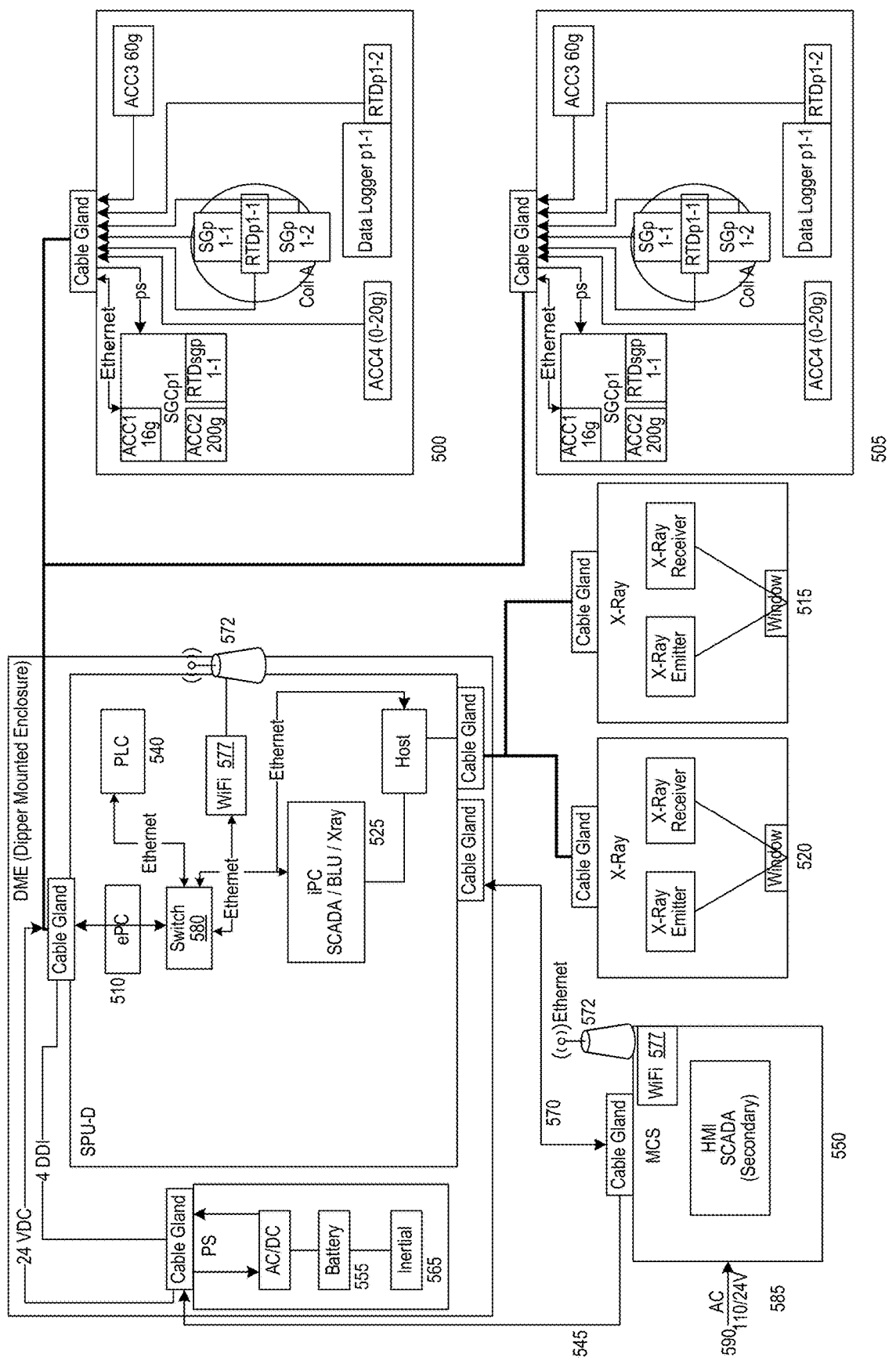
FIG. 5 is a schematic illustration of power and in accordance with various embodiments described herein.

With reference now to FIG. 5, an implementation of various embodiments of the mining shovel bucket described herein is shown. In cheek sensors 500 and 505 are connected to an electronic data processor or ePC 510 for digital processing of the sensor signals. Down looking sensors 515 and 520 are connected to ePC 525 for digital processing of the sensor signals. Signals from in-cheek sensors 500, 505, and down-looking sensors 515, 520 are processed via ePC 525 where results are compared to predetermined spectra for evaluation. All operations of sensors, ePCs, and other ancillaries are controlled by PLC 540. AC power from chassis enclosure 550 is delivered by AC power cable 545. Backup power is supplied by battery 555, which can be recharged when offline from AC power via inertial recharging system 565. Communication between the dipper mounted enclosure and chassis enclosure 550 is maintained by fibre optic ethernet link 570 as well as wireless communication 572. Wireless signals are received by wireless access point 577 and/or via ethernet link via switch 580. Power is supplied from shovel 590 to chassis enclosure 550 via AC power cable 585.

Figure 6:
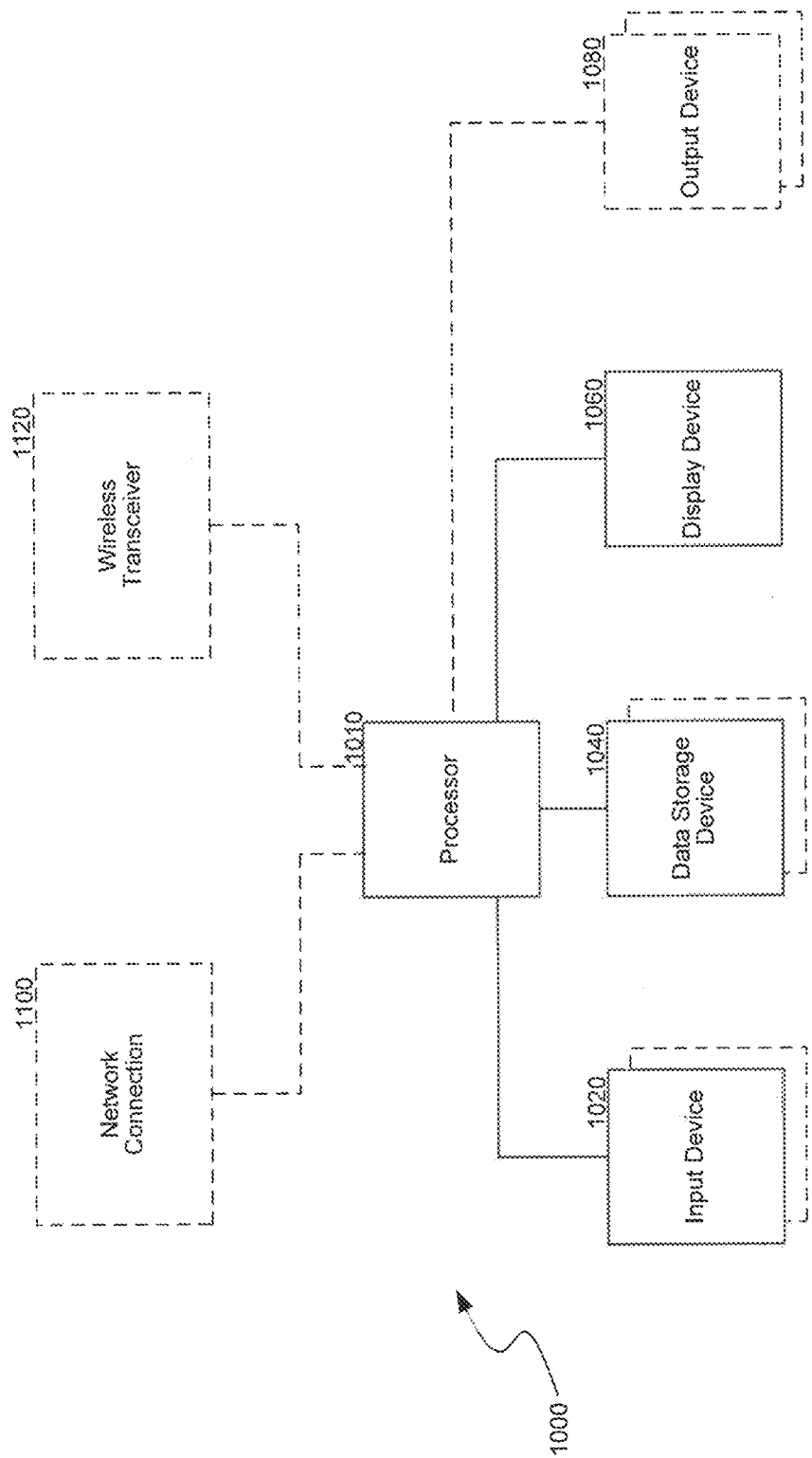
FIG. 6 is a block diagram of a basic and suitable computer that may employ aspects of the various embodiments described herein.

FIG. 6 and the following discussion provide a brief, general description of a suitable computing environment in which aspects of the disclosed system can be implemented. Although not required, aspects and embodiments of the disclosed system will be described in the general context of computer-executable instructions, such as routines executed by a general-purpose computer, e.g., a server or personal computer. Those skilled in the relevant art will appreciate that the various embodiments can be practiced with other computer system configurations, including Internet appliances, hand-held devices, wearable computers, cellular or mobile phones, multi-processor systems, microprocessor-based or programmable consumer electronics, set-top boxes, network PCs, mini-computers, mainframe computers and the like. The embodiments described herein can be embodied in a special purpose computer or data processor that is specifically programmed, configured or constructed to perform one or more of the computer-executable instructions explained in detail below. Indeed, the term "computer" (and like terms), as used generally herein, refers to any of the above devices, as well as any data processor or any device capable of communicating with a network, including consumer electronic goods such as game devices, cameras, or other electronic devices having a processor and other components, e.g., network communication circuitry.

The embodiments described herein can also be practiced in distributed computing environments, where tasks or modules are performed by remote processing devices, which are linked through a communications network, such as a Local Area Network ("LAN"), Wide Area Network ("WAN") or the Internet. In a distributed computing environment, program modules or sub-routines may be located in both local and remote memory storage devices. Aspects of the system described below may be stored or distributed on computer-readable media, including magnetic and optically readable and removable computer discs, stored as in chips (e.g., EEPROM or flash memory chips). Alternatively, aspects of the system disclosed herein may be distributed electronically over the Internet or over other networks (including wireless networks). Those skilled in the relevant art will recognize that portions of the embodiments described herein may reside on a server computer, while corresponding portions reside on a client computer. Data structures and transmission of data particular to aspects of the system described herein are also encompassed within the scope of this application.

Referring to FIG. 6, one embodiment of the system described herein employs a computer 1000, such as a personal computer or workstation, having one or more processors 1010 coupled to one or more user input devices 1020 and data storage devices 1040. The computer is also coupled to at least one output device such as a display device 1060 and one or more optional additional output devices 1080 (e.g., printer, plotter, speakers, tactile or olfactory output devices, etc.). The computer may be coupled to external computers, such as via an optional network connection 1100, a wireless transceiver 1120, or both.

The input devices 1020 may include a keyboard and/or a pointing device such as a mouse. Other input devices are possible such as a microphone, joystick, pen, game pad, scanner, digital camera, video camera, and the like. The data storage devices 1040 may include any type of computer-readable media that can store data accessible by the computer 1000, such as magnetic hard and floppy disk drives, optical disk drives, magnetic cassettes, tape drives, flash memory cards, digital video disks (DVDs), Bernoulli cartridges, RAMs, ROMs, smart cards, etc. Indeed, any medium for storing or transmitting computer-readable instructions and data may be employed, including a connection port to or node on a network such as a local area network (LAN), wide area network (WAN) or the Internet (not shown in FIG. 6).

Figure 7:
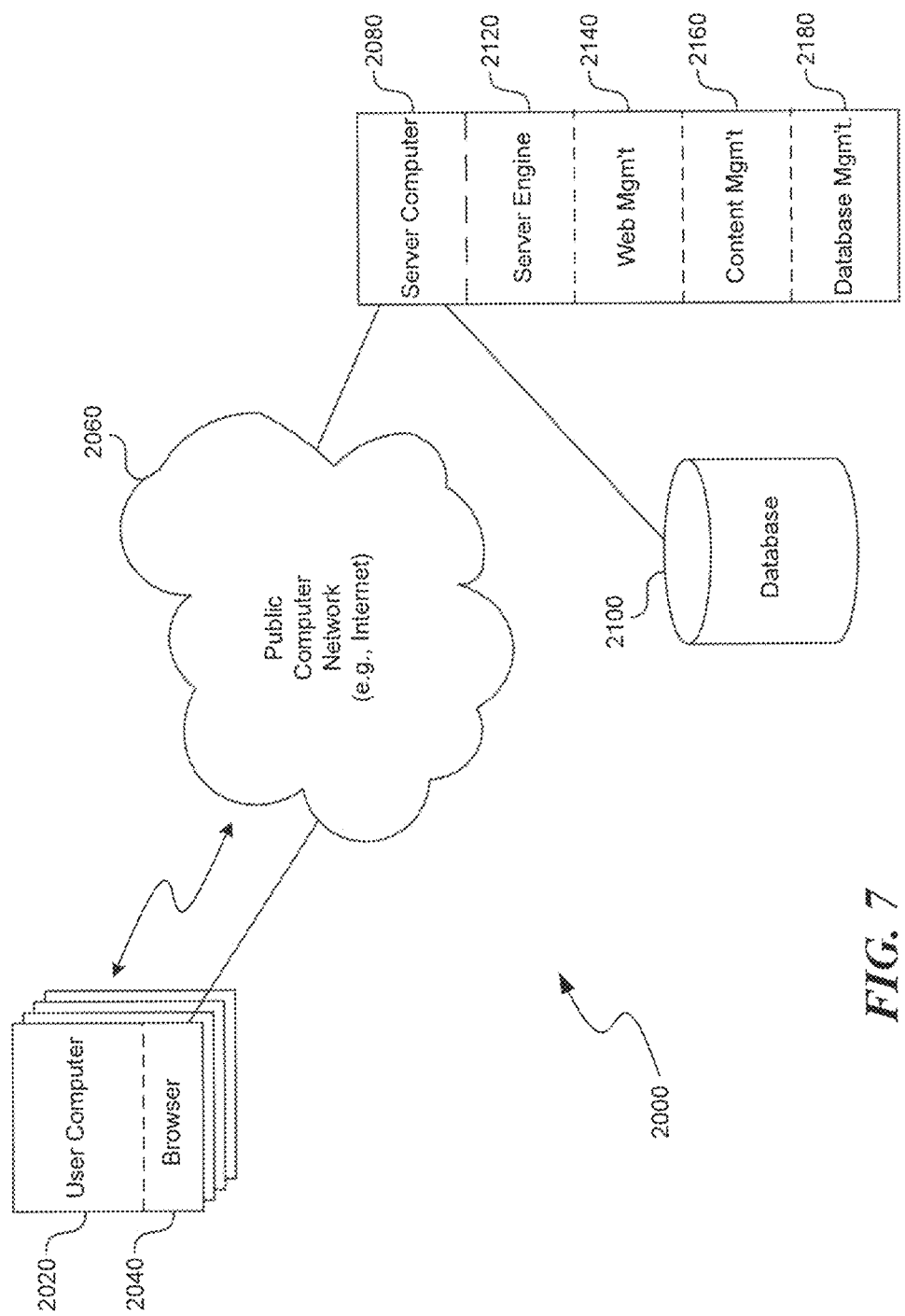
FIG. 7 is a block diagram illustrating a simple, yet suitable system in which aspects of the various embodiments described herein may operate in a networked computer environment.

Aspects of the system described herein may be practiced in a variety of other computing environments. For example, referring to FIG. 7, a distributed computing environment with a web interface includes one or more user computers 2020 in a system 2000 are shown, each of which includes a browser program module 2040 that permits the computer to access and exchange data with the Internet 2060, including web sites within the World Wide Web portion of the Internet. The user computers may be substantially similar to the computer described above with respect to FIG. 6. User computers may include other program modules such as an operating system, one or more application programs (e.g., word processing or spread sheet applications), and the like. The computers may be general-purpose devices that can be programmed to run various types of applications, or they may be single-purpose devices optimized or limited to a particular function or class of functions. More importantly, while shown with web browsers, any application program for providing a graphical user interface to users may be employed, as described in detail below; the use of a web browser and web interface are only used as a familiar example here.

At least one server computer 2080, coupled to the Internet or World Wide Web ("Web") 2060, performs much or all of the functions for receiving, routing and storing of electronic messages, such as web pages, audio signals, and electronic images. While the Internet is shown, a private network, such as an intranet may indeed be preferred in some applications. The network may have a client-server architecture, in which a computer is dedicated to serving other client computers, or it may have other architectures such as a peer-to-peer, in which one or more computers serve simultaneously as servers and clients. A database 2100 or databases, coupled to the server computer(s), stores much of the web pages and content exchanged between the user computers. The server computer(s), including the database(s), may employ security measures to inhibit malicious attacks on the system, and to preserve integrity of the messages and data stored therein (e.g., firewall systems, secure socket layers (SSL), password protection schemes, encryption, and the like).

The server computer 2080 may include a server engine 2120, a web page management component 2140, a content management component 2160 and a database management component 2180. The server engine performs basic processing and operating system level tasks. The web page management component handles creation and display or routing of web pages. Users may access the server computer by means of a URL associated therewith. The content management component handles most of the functions in the embodiments described herein. The database management component includes storage and retrieval tasks with respect to the database, queries to the database, and storage of data.

In general, the detailed description of embodiments of the invention is not intended to be exhaustive or to limit the invention to the precise form disclosed above. While specific embodiments of, and examples for, the invention are described above for illustrative purposes, various equivalent modifications are possible within the scope of the invention, as those skilled in the relevant art will recognize. For example, while processes or blocks are presented in a given order, alternative embodiments may perform routines having steps, or employ systems having blocks, in a different order, and some processes or blocks may be deleted, moved, added, subdivided, combined, and/or modified. Each of these processes or blocks may be implemented in a variety of different ways. Also, while processes or blocks are at times shown as being performed in series, these processes or blocks may instead be performed in parallel, or may be performed at different times.

Aspects of the invention may be stored or distributed on computer-readable media, including magnetically or optically readable computer discs, hard-wired or preprogrammed chips (e.g., EEPROM semiconductor chips), nanotechnology memory, biological memory, or other data storage media. Alternatively, computer implemented instructions, data structures, screen displays, and other data under aspects of the invention may be distributed over the Internet or over other networks (including wireless networks), on a propagated signal on a propagation medium (e.g., an electromagnetic wave(s), a sound wave, etc.) over a period of time, or they may be provided on any analog or digital network (packet switched, circuit switched, or other scheme). Those skilled in the relevant art will recognize that portions of the invention reside on a server computer, while corresponding portions reside on a client computer such as a mobile or portable device, and thus, while certain hardware platforms are described herein, aspects of the invention are equally applicable to nodes on a network.

The teachings of the invention provided herein can be applied to other systems, not necessarily the system described herein. The elements and acts of the various embodiments described herein can be combined to provide further embodiments.

Any patents, applications and other references, including any that may be listed in accompanying filing papers, are incorporated herein by reference. Aspects of the invention can be modified, if necessary, to employ the systems, functions, and concepts of the various references described above to provide yet further embodiments of the invention.

These and other changes can be made to the invention in light of the above Detailed Description. While the above description details certain embodiments of the invention and describes the best mode contemplated, no matter how detailed the above appears in text, the invention can be practiced in many ways. Details of the invention may vary considerably in its implementation details, while still being encompassed by the invention disclosed herein. As noted above, particular terminology used when describing certain features or aspects of the invention should not be taken to imply that the terminology is being redefined herein to be restricted to any specific characteristics, features, or aspects of the invention with which that terminology is associated. In general, the terms used in the following claims should not be construed to limit the invention to the specific embodiments disclosed in the specification, unless the above Detailed Description section explicitly defines such terms. Accordingly, the actual scope of the invention encompasses not only the disclosed embodiments, but also all equivalent ways of practicing or implementing the invention.

We claim:

1. A mining shovel bucket system comprising:
a mining shovel bucket; and
at least one down-looking sensor positioned on an upper wall portion of, and at a mouth of, the mining shovel bucket;
wherein the at least one down-looking sensor is configured to collect data regarding at least one characteristic of mining material handled by the mining shovel bucket.

2. The mining shovel bucket system of claim 1, wherein the at least one down-looking sensor comprises a first down-looking sensor positioned in a forward portion of the upper wall portion and a second down-looking sensor positioned in an aft portion of the upper wall portion.

3. The mining shovel bucket system of claim 1, wherein the at least one down-looking sensor is configured to collect data related to the composition of the mining material handled by the bucket.

4. The mining shovel bucket system of claim 1, further comprising a control enclosure housing at least one of: a signal processing system configured to receive and process signals transmitted by the at least one down-looking sensor; a power supply for the at least one down-looking sensor, the signal processing system, or both; and a communications system configured to transmit information generated by the signal processing system to a location remove from the mining shovel bucket.

5. The mining shovel bucket system of claim 1, wherein the at least one down-looking sensor comprises a first down-looking sensor configured to collect data relating to a first characteristic of the mining material handled by the mining shovel bucket system and a second down-looking sensor configured to collect data relating to a second characteristic of the mining material handled by the mining shovel bucket system, and the first characteristic is different from the second characteristic.

6. A method of classifying and sorting mining material comprising:
sensing mining material handled by a mining shovel bucket using at least down-looking sensor mounted on a top wall portion of the mining shovel bucket,
wherein the at least one down-looking sensor is configured to collect data regarding at least one characteristic of mining material handled by the mining shovel bucket;
identifying the characteristic of the mining material using data gathered from sensing the mining material; and
depositing the mining material in a specific location based on the characteristic of the mining material.

7. The method of claim 6, wherein the characteristic is the composition of the mining material and identifying the composition of the mining material comprises:
transmitting the data to an analogue to digital signal converter to convert the data to a digital signal;
performing Fourier Analysis on the digital signal to generate arbitrary power spectra data;
comparing the arbitrary power spectra data to known power spectra to identify pattern matching between the arbitrary power spectra and known power spectra; and
identifying the composition of the mineral material when a sufficient pattern match is identified between the arbitrary power spectra and a known power spectra associated with a known material.

8. The method of claim 7, wherein the arbitrary power spectra is of amplitude/frequency or amplitude/wavelength.

9. The method of claim 6, wherein identifying the characteristic of the mining material takes place at location remote from the mining shovel bucket, and wherein an instruction is sent to a mining shovel operator from the remote location after the mining material has been identified instructing the mining shovel operator where to deposit the mining material.

10. The mining shovel bucket system of claim 1 further comprising a control system coupled to the at least one down-looking sensor and configured to:
transmit the data to an enterprise resource planning (ERP) system located remote from the mining shovel, the ERP system being configured to receive the data from the at least one down-looking sensor and analyze the data to identify the characteristic of the mining material handled by the mining shovel bucket; and receive instructions regarding where to deposit mining material loaded in the mining shovel bucket based on the characteristic information from a fleet management system located remote from the mining shovel bucket and the ERP system, the fleet management system being configured to receive characteristic information from the ERP system and transmit instructions to the mining shovel bucket.

11. The mining shovel bucket system of claim 10, wherein the mining shovel bucket is configured to transmit the data to the ERP system over a wireless network.

12. The mining shovel bucket system of claim 10, wherein the mining shovel bucket is associated with a chassis further comprising a local display located within the chassis, and wherein the instructions from the fleet management system are displayed on the local display.

13. The mining shovel bucket system of claim 1, wherein the at least one down-looking sensor comprises a first down-looking sensor in a first position on the upper wall portion and a second down-looking sensor in a second position on the upper wall portion, wherein the second position is to the side of the first position.

14. The mining shovel bucket system of claim 1, wherein the at least one down-looking sensor is configured to collect data related to the chemical composition of the mining material handled by the mining shovel bucket system.

15. The mining shovel bucket system of claim 1, wherein the at least one down-looking sensor is configured to collect data related to the quality of the mining material handled by the mining shovel bucket system.

16. The mining shovel bucket system of claim 1, wherein the at least one down-looking sensor is configured to collect data related to the content of undesired material in the mining material handled by the mining shovel bucket system.

17. The mining shovel bucket system of claim 5, wherein the first down-looking sensor is a different type of sensor from the second down-looking sensor.

18. The mining shovel bucket system of claim 4, wherein the control enclosure is secured to a top of the mining shovel bucket.

19. The mining shovel bucket system of claim 4, wherein the control enclosure is positioned remove from the mining shovel bucket.

20. The mining shovel bucket system of claim 1, wherein the at least one down-looking sensor faces towards a lower wall portion of the mining shovel bucket, the lower wall portion being opposite the upper wall portion.

21. A mining shovel bucket system comprising: a bucket having an upper wall portion and a mouth; and a sensor for downward sensing from the upper wall portion of the bucket, wherein the sensor is positioned on the upper wall portion and at the mouth of the bucket; wherein the sensor is configured to collect data regarding at least one characteristic of mining material within the bucket.

22. The mining shovel bucket system of claim 1, further comprising an in-cheek sensor positioned on a sidewall of the mining shovel bucket and configured to detect data regarding characteristics of mining material received in the mining shovel bucket.

23. The mining shovel bucket system of claim 21 wherein the sensor means is positioned at an interior portion of the bucket means.

* * * * *